United States Patent [19]
Mattiessen

[11] Patent Number: 5,183,550
[45] Date of Patent: * Feb. 2, 1993

[54] MEASURING CELL FOR ELECTROCHEMICALLY DETECTING A GAS

[75] Inventor: Hans Mattiessen, Bad Schwartau, Fed. Rep. of Germany

[73] Assignee: Drägerwerk Aktiengesellschaft, Lübeck, Fed. Rep. of Germany

[*] Notice: The portion of the term of this patent subsequent to Jan. 29, 2008 has been disclaimed.

[21] Appl. No.: 541,942

[22] Filed: Jun. 22, 1990

[30] Foreign Application Priority Data

Jun. 30, 1989 [DE] Fed. Rep. of Germany ....... 3921528

[51] Int. Cl.$^5$ .................................... G01N 27/404
[52] U.S. Cl. .................. 204/415; 204/153.17; 204/412
[58] Field of Search ................ 204/153.17, 412, 415

[56] References Cited

U.S. PATENT DOCUMENTS

| | | |
|---|---|---|
| 3,410,778 | 11/1968 | Krasberg ................ 204/415 |
| 3,518,179 | 6/1970 | Bleak et al. ............. 204/415 |
| 3,575,836 | 4/1971 | Sternberg ............... 204/415 |
| 3,755,125 | 8/1973 | Shaw et al. ............. 204/415 |
| 3,855,096 | 12/1974 | Bergman ................ 204/415 |
| 4,367,133 | 1/1983 | Lauer ..................... 204/415 |
| 4,474,648 | 10/1984 | Tantram et al. ......... 204/415 |
| 4,655,900 | 4/1987 | Neti et al. .............. 204/415 |
| 4,695,361 | 9/1987 | Grady ..................... 204/415 |
| 4,775,456 | 10/1988 | Shah et al. .............. 204/415 |
| 4,790,925 | 12/1988 | Miller et al. ............ 204/415 |
| 4,948,496 | 8/1990 | Chand .................... 204/415 |
| 4,988,429 | 1/1991 | Matthiessen ............ 204/415 |

FOREIGN PATENT DOCUMENTS 227029 4/1985 Fed. Rep. of Germany .
1344616 1/1974 United Kingdom .
2094005 9/1982 United Kingdom .

OTHER PUBLICATIONS

Fischer et al., *Trans. Am. Soc. Artif. Intern. Organs*, 28:245–248, (1982).

Primary Examiner—T. Tung
Attorney, Agent, or Firm—Walter Ottesen

[57] ABSTRACT

The invention is directed to a measuring cell for electrochemically detecting a gas sample and has at least one measuring electrode and one counter electrode disposed in a housing defining a chamber filled with an electrolyte. The measuring cell also includes a protective disc which is at least partially permeable and is improved so that the configuration of the measuring cell is substantially simpler and is of reduced volume without reducing the ion mobility in the electrolyte and with a significant supply of the electrolyte. The counter electrode is in the form of a layer and is applied to a region of the protective disc facing toward the electrolyte. this region is impermeable to the gas sample and the electrolyte. The counter electrode is further electrically insulated from the measuring electrode and is in permanent contact with the electrolyte. Only the measuring electrode and the diffusion membrane are applied to a region of the protective disc which is permeable to the gas sample.

3 Claims, 1 Drawing Sheet

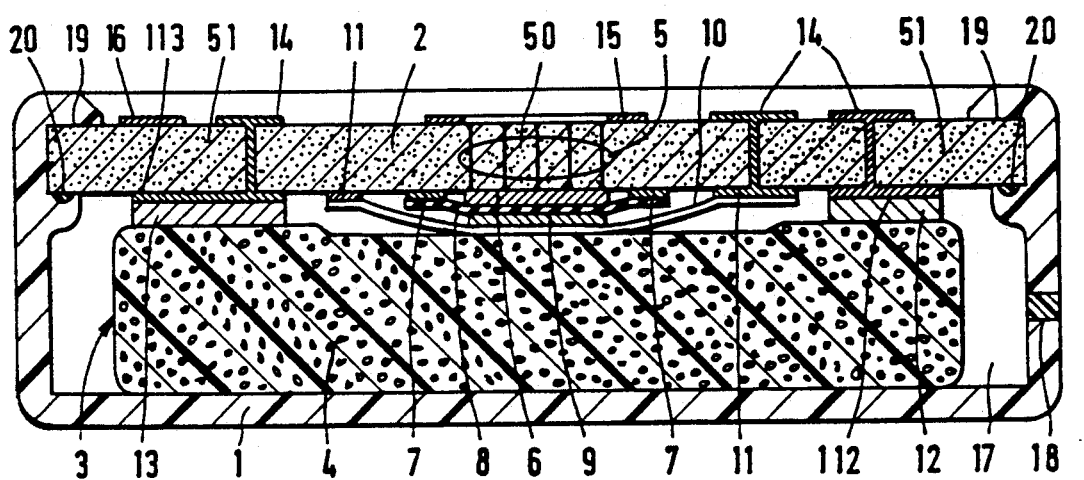

MEASURING CELL FOR ELECTROCHEMICALLY DETECTING A GAS

FIELD OF THE INVENTION

The invention relates to a measuring cell for electrochemically detecting a gaseous sample. The measuring cell defines an electrolyte chamber filled with an electrolyte and has at least one measuring electrode and one counter electrode. The cell also includes a diffusion membrane having an inner surface facing toward the electrolyte. The diffusion membrane is impermeable to the electrolyte and permeable to the gas sample. The measuring electrode is in the form of a layer and is applied to the inner surface of the membrane. The diffusion membrane has an outer surface facing toward the gas sample and the measuring cell includes a partially permeable protective disc covering the diffusion membrane at the outer side thereof.

BACKGROUND OF THE INVENTION

A measuring cell of the kind described above is disclosed in British Patent 1,344,616.

The known measuring cell includes an electrolyte chamber accommodating the measuring electrode and the counter electrode. The measuring electrode is applied as an electrically-conductive layer to the back surface of a diffusion membrane facing the electrolyte. The diffusion membrane is protected on the side thereof facing the ambient against mechanical influences by a permeable protective disc. It is necessary to provide an adequately large supply of electrolyte in order that measuring cells of the above-mentioned type are operationally and measurement ready over an adequately long time duration. The charge carriers generated at the boundary interface "electrolyte/measuring electrode/gas sample" diffuse in the electrolyte supply between the measuring electrode and the counter electrode. Accordingly, a good ion mobility is required for an adequate response time for measuring cells of this type to thereby prevent the premature exsiccation or concentration of the electrolyte. This increases the size of such measuring cells so that especially portable measuring apparatus become inconvenient to handle.

Published British patent application 2,094,005 discloses that the electrodes in the form of layers are brought as close to each other as possible. This compact electrode arrangement is however achieved with a complex wick configuration which makes it possible to bring the necessary electrolyte to the surface of the measuring electrode from the electrolyte supply.

SUMMARY OF THE INVENTION

It is an object of the invention to improve a measuring cell of the kind described above so that the construction of the measuring cell is substantially simpler with a significant electrolyte supply. It is another object of the invention to provide such a measuring cell having a reduced volume without reducing the ion mobility in the electrolyte.

The measuring cell of the invention is for electrochemically detecting a gas sample. The measuring cell includes: a housing having an opening directed toward the gas sample to be detected and defining an electrolyte chamber; an electrolyte contained in the chamber; a measuring electrode and a counter electrode disposed in the chamber so as to be in spaced relationship to each other; a diffusion membrane interposed between the opening and the electrolyte and being permeable to the gas sample; the diffusion membrane being impermeable to the electrolyte and having a lower surface facing the electrolyte; the measuring electrode being configured as a measuring electrode layer applied to the lower surface of the membrane; the membrane having an upper surface facing toward the gas sample; a protective disc interposed between the opening and the upper surface of the diffusion membrane; the protective disc having a first component region permeable to the gas sample and a second component region impermeable to the gas sample and to the electrolyte; the second component region having a lower surface area facing toward the electrolyte and the counter electrode being configured as a counter electrode layer applied to the lower surface area of the second component region; the counter electrode layer being electrically isolated from the measuring electrode and being in permanent electrical contact with the electrolyte; and, the measuring electrode layer and the diffusion membrane being applied to the first component region of the protective disc.

According to a feature of the measuring cell of the invention, the counter electrode is in the form of a layer and is applied to a component region of the protective disc which is impermeable to the electrolyte and to the gas sample. The counter electrode is electrically insulated from the measuring electrode and is in permanent contact with the electrolyte. Only the measuring electrode together with the diffusion membrane is applied to a region of the protective disc which is permeable to the gas sample.

The advantage of the invention is seen essentially in that the measuring electrode as well as the counter electrode are mounted next to each other in a close spatial arrangement and are in direct contact with the electrolyte. In this way, a short diffusion path makes a rapid response time possible with very high measuring gas concentrations. A small construction volume of the measuring cell is made possible by the layer-like arrangement on one and the same surface of the protective disc. The electrolyte supply can be extended and prevents an exsiccation of the electrolyte even with longer operating durations.

If it is intended to operate the measuring cell in a potentiostatic operating mode, then the required reference electrode can be placed in the same manner directly adjacent to the remaining electrodes in the form of a layer on the electrolyte side of the protective disc.

During operation with or without the reference electrode, the permeability of the protective disc is only provided in that region which lies opposite the measuring electrode. The gas to be investigated passes through the protective disc in its permeable region and diffuses through the membrane as well as the permeable measuring cell to the contact interface "electrolyte/measuring electrode/gas sample". It can be necessary to catalytically convert the gas sample at the electrolyte side into such components which lead to an electrochemical reaction because of the applied measuring cell voltage. For this purpose, the measuring electrode can be provided with a catalytic additive.

A further advantage is provided in that the measuring cell can be operated in any desired position because of the permanent electrolyte contact to the measuring electrode.

It is especially advantageous to manufacture the protective disc from a thermally-conductive electrically-insulating material and to determine the permeable region with passages which specify the diffusion of the gas sample. The impermeable component region of the protective disc facing the ambient containing the gas sample carries electric contact pads which are contacted through to the electrodes. With these features, an advantageous temperature compensation for all of the electrodes disposed on the electrolyte side of the protective disc is obtained so that the temperature movement of the measuring result is avoided. At the same time, the measuring cell can operate in the limiting diffusion current region with the limiting diffusion current being determined by the dimensions of the passages in coaction with the electrode activity. The passages can, for example, be configured as long and narrow diffusion channels.

Since the material of the protective disc is electrically insulating, a through-contact is possible in a simple manner which provides for an electrical connection of the electrodes to the surface of the protective disc facing the ambient. A simple take-off of the measuring signal to an evaluation apparatus can be realized by a simple bonding of the connecting leads to the contact pads of the upper surface.

Another possibility is that the connection to the contact pads during assembly of the measuring cell can be produced in a suitable housing by appropriate contact pads functioning as measuring signal take-offs. In both cases, the need for passing the lead connections from the electrodes through the measuring cell housing is avoided. This contributes to a significant increase in the operational reliability of the measuring cell since slow leaks of the electrolyte which are difficult to control and extend along the lead pass-throughs to the contacts are avoided.

A contact mat made of a formed graphite fabric is provided in order to realize a nearly uniform contacting of the measuring electrode as possible. The contact mat is on the one hand placed over the measuring electrode on the side thereof facing the electrolyte and, on the other hand, is led to the measuring contacts provided therefor on the side of the impermeable component region facing the electrolyte. The measuring electrode is then packed between the diffusion membrane and the permeable contact mat in a sandwich configuration. In this way, the application of electrical contacts for the measuring electrode on the thin and tear sensitive diffusion membrane is avoided and a large-surface contact is provided.

To improve handling of the electrolyte, it is advantageously held in an absorbent body which fills out the electrolyte chamber and is in permanent contact with the electrodes. The only boundary of the measuring cell to the ambient is defined by the protective disc. The absorbent body can be made of a sponge-like polyethylene body so that a simple configuration can be selected for the measuring cell housing without it being necessary to attend to special sealing problems associated with liquids. For example, the necessary ventilating openings in the electrolyte chamber can be provided without the necessity of additional sealing measures with respect to the liquid.

The protective disc is made of a thermally-conductive material and has an outer surface facing toward the ambient. For this configuration it is especially advantageous to apply a temperature-sensitive element to this outer surface at least around the permeable region or even thereacross. In this way, it is possible to detect almost precisely the temperature of the gas sample present in the diffusion region and to then carry out a subsequent compensation of the measured value. It can be assumed that the gas sample has taken on the temperature of the sealing disc with sufficient accuracy during the diffusion through the permeable region. In this way, the temperature of the protective disc is suitable as a corrective factor to a good approximation.

The sealing disc can also advantageously be used as a carrier for a preamplifier circuit formed with hybrid technology. This leads to a further miniaturization of the measuring cell and increases the signal-to-noise ratio.

According to another feature of the invention, a porous gas distribution layer is arranged behind the passages facing toward the membrane on the electrolyte side in order to improve the distribution of the gas sample (diffusing through the permeable region) on the surface of the diffusion membrane. This gas distribution layer is held by the diffusion membrane thermally welded to the surface of the sealing disc facing the electrolyte. A suitable method for thermally welding the diffusion membrane made, for example, of polytetrafluoroethylene (PTFE) to a metallic or ceramic protective disc is disclosed in published German examined patent application 2,311,096.

BRIEF DESCRIPTION OF THE DRAWING

The invention will now be described with reference to the single figure of the drawing which shows an embodiment of a measuring cell of the invention, in section, but not drawn to scale because of its actual miniature size and the components thereof have increased dimensions to clearly show their relationship to each other.

DESCRIPTION OF THE PREFERRED EMBODIMENTS OF THE INVENTION

The measuring cell includes a pot-shaped housing 1 made of plastic which is of circular shape. The measuring cell has an opening facing the ambient which is covered by a protective disc 2 made of ceramic. The inner chamber of the housing 1 is essentially filled by an absorbent body 3 made of polyethylene in which the electrolyte 4 is accommodated. The ceramic disc 2 is penetrated in the center by a plurality of passages 5. The passages 5 have funnel-shaped inlets and outlets and are otherwise configured as capillary tubes which determine the diffusion rate of the gas sample diffusing into the measuring cell from the ambient. The passages are shown by simple lines because of their reduced diameter. The geometric location of the passages 5 defines the permeable region 50 of the protective disc 2.

The component region 51 surrounding the permeable region 50 and extending to the edge of the circularly-shaped protective disc 2 defines the impermeable region of the protective disc 2. A gas distribution layer 6 is attached over the outlets of the passages 5 on the electrolyte side of the protective disc 2 behind the passages 5. This gas distribution layer 6 covers a diffusion membrane 8 which is attached to the weld edge 7. The diffusion membrane 8 carries the measuring electrode 9 over which a contact mat 10 is pulled to the absorbent body 3. The contact mat 10 is made of a formed graphite fabric and is permeable The contact mat 10 realizes a nearly uniform contacting of the measuring electrode 9 as possible and is bonded to the measuring contacts 11. A counter electrode 12 and a reference electrode 13 are applied to their respective contact pads (112, 113) also at the electrolyte side on the inner surface of the protective, disc 2. The contact mat 10 as well as the contact pads (112, 113) of the counter electrode 12 and the reference electrode 13, respectively, are in electrical contact with the absorbent body 3.

The measuring contact 11 as well as the contact pads (112, 113) are connected through to work contacts 14 on the outer surface of the protective disc 2 facing the ambient. A ring-shaped temperature-sensitive element 15 in the form of an NTC-resistor is applied to this outer surface of the protective disc 2 in surrounding relationship to the passages 5 of the permeable region 50. An amplifier circuit 16 is schematically represented in the drawing and is disposed at the edge of the impermeable region 51. The amplifier circuit 16 can be applied utilizing thin-film technology. The electrical signals from the work contact pads 14 as well as from the temperature-sensitive element 15 are conducted to this preamplifier circuit 16 via connecting leads (not shown) and processed before these signals are conducted to an evaluation and measuring unit (not shown).

The housing 1 is made of pliant plastic with the electrolyte chamber being connected with the ambient via a compensating opening 18. The protective disc 2 defines the boundary of the housing facing the gas atmosphere to be investigated. The protective disc can be held in a peripheral snap recess 19 and sealed with respect to the electrolyte chamber 17 by an O-ring 20.

It is understood that the foregoing description is that of the preferred embodiments of the invention and that various changes and modifications may be made thereto without departing from the spirit and scope of the invention as defined in the appended claims.

What is claimed is:

1. A measuring cell for electrochemically detecting a gas sample, the measuring cell comprising:
    a housing having an opening directed toward the gas sample to be detected and defining an electrolyte chamber;
    an electrolyte contained in said chamber;
    a measuring electrode and an counter electrode disposed in said chamber so as to be in spaced relationship to each other;
    a diffusion membrane interposed between aid opening and said electrolyte and being permeable to the gas sample;
    said diffusion membrane being impermeable to said electrolyte and having a lower surface facing said electrolyte;
    said measuring electrode being configured as a measuring electrode layer applied to said lower surface of said diffusion membrane;
    said diffusion membrane having an upper surface facing toward the gas sample;
    a protective disc interposed between said opening and said upper surface of said diffusion membrane;
    said protective disc having a first component region permeable to the gas sample and a second component region impermeable to the gas sample and to said electrolyte;
    said first component region having an upper surface area directed toward the gas sample and a lower surface area facing toward said electrolyte;
    said first component region including a plurality of capillary passages formed in said protective disc and extending between said upper and lower surface areas of said first component region;
    said second component region having a lower surface area facing toward said electrolyte and said counter electrode being configured as a counter electrode layer applied to said lower surface area of said second component region;
    said counter electrode layer being electrically isolated from said measuring electrode and being in permanent electrical contact with said electrolyte;
    said measuring electrode layer and said diffusion membrane being applied to said lower surface area of said first component region of said protective disc so as to communicate with said capillary passages;
    said protective disc being made of thermally-conductive electrically-insulating material;
    said capillary passages being dimensioned to determined the diffusion of the gas sample;
    said second component region having an upper surface area facing the gas sample; and,
    the measuring cell further comprising working contact pads formed on said upper surface area of said second component region and being connected through said protective disc to respective ones of said electrodes.

2. The measuring cell of claim 1, further comprising: a contact mat for interconnecting said measuring electrode layer to the one working contact pad corresponding thereto; an ancillary measuring contact applied to said lower surface area of said second component region and being through connected to said one working contact; and said contact mat extending over said measuring electrode layer between said measuring electrode layer and said electrolyte and being connected to said ancillary measuring contact.

3. A measuring cell for electrochemically detecting a gas sample, the measuring cell comprising:
    a housing having an opening directed toward the gas sample to be detected and defining an electrolyte chamber;
    an electrolyte contained in said chamber;
    a measuring electrode and a counter electrode disposed in said chamber so as to be in spaced relationship to each other;
    a diffusion membrane interposed between said opening and said electrolyte and being permeable to the gas sample;
    said diffusion membrane being impermeable to said electrolyte and having a lower surface facing said electrolyte;
    said measuring electrode being configured as a measuring electrode layer applied to said lower surface of said diffusion membrane;
    said diffusion membrane having an upper surface facing toward the gas sample;
    a protective disc made of ceramic and being interposed between said opening and said upper surface of said diffusion membrane;
    said protective disc having a first component region permeable to the gas sample and a second component region impermeable to the gas sample and to said electrolyte;
    said first component region having an upper surface area directed toward the gas sample and a lower surface area facing toward said electrolyte;
    said first component region including a plurality of capillary passages formed in said protective disc and extending between said upper and lower surface areas of said first component region;

said second component region having a lower surface area facing toward said electrolyte and said counter electrode being configured as a counter electrode layer applied to said lower surface area of said second component region;

said counter electrode layer being electrically isolated from said measuring electrode and being in permanent electrical contact with said electrolyte; and said measuring electrode layer and said diffusion membrane being applied to said lower surface area of said first component region of said protective disc so as to communicate with said capillary passages.

* * * * *

UNITED STATES PATENT AND TRADEMARK OFFICE
CERTIFICATE OF CORRECTION

PATENT NO. : 5,183,550
DATED : February 2, 1993
INVENTOR(S) : Hans Matthiessen

It is certified that error appears in the above-identified patent and that said Letters Patent is hereby corrected as shown below:

On the title page, in the abstract, line 12: delete "this" and substitute -- This -- therefor.

In column 5, line 3: delete the comma between "protective" and "disc 2".

In column 5, line 19, delete "preamplifier" and substitute -- amplifier -- therefor.

In column 5, line 43, delete "an" and substitute -- a -- therefor.

In column 5, line 45, delete "aid" and substitute -- said -- therefor.

In column 6, lines 16 and 17, delete "determined" and substitute -- determine -- therefor.

Signed and Sealed this

Twenty-first Day of June, 1994

Attest:

BRUCE LEHMAN

Attesting Officer     Commissioner of Patents and Trademarks